(12) United States Patent
Peglion et al.

(10) Patent No.: US 8,097,720 B2
(45) Date of Patent: Jan. 17, 2012

(54) PROCESS FOR THE SYNTHESIS OF IVABRADINE AND ADDITION SALTS THEREOF WITH A PHARMACEUTICALLY ACCEPTABLE ACID

(75) Inventors: Jean-Louis Peglion, Le Vesinet (FR); Aimee Dessinges, Rueil Malmaison (FR); Bernard Serkiz, Servon Brie Comte Robert (FR); Jean-Michel Lerestif, Yvetot (FR); Jean-Pierre Lecouve, Le Havre (FR)

(73) Assignee: Les Laboratoires Server, Suresnes Cedex (FR)

( * ) Notice: Subject to any disclaimer, the term of this patent is extended or adjusted under 35 U.S.C. 154(b) by 266 days.

(21) Appl. No.: 12/655,087

(22) Filed: Dec. 23, 2009

(65) Prior Publication Data

US 2010/0160628 A1    Jun. 24, 2010

(30) Foreign Application Priority Data

Dec. 24, 2008    (FR) ..................................... 08 07444

(51) Int. Cl.
C07D 223/16    (2006.01)
C07C 47/575    (2006.01)

(52) U.S. Cl. ....................................... 540/523; 568/441
(58) Field of Classification Search .................. 540/523; 568/441

See application file for complete search history.

(56) References Cited

FOREIGN PATENT DOCUMENTS

WO    WO 2008/065681    6/2008
WO    WO 2008/146308    12/2008

OTHER PUBLICATIONS

French Preliminary Search Report for FR0807444 of Jul. 10, 2009.

*Primary Examiner* — Bruck Kifle
(74) *Attorney, Agent, or Firm* — Hueschen and Sage

(57) ABSTRACT

Process for the synthesis of ivabradine of formula (I):

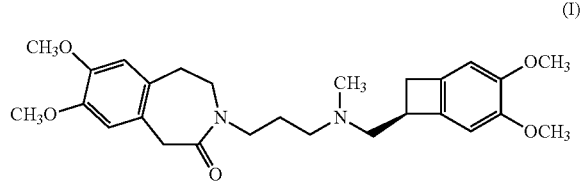

and addition salts thereof with a pharmaceutically acceptable acid.

14 Claims, No Drawings

PROCESS FOR THE SYNTHESIS OF IVABRADINE AND ADDITION SALTS THEREOF WITH A PHARMACEUTICALLY ACCEPTABLE ACID

The present invention relates to a process for the synthesis of ivabradine of formula (I):

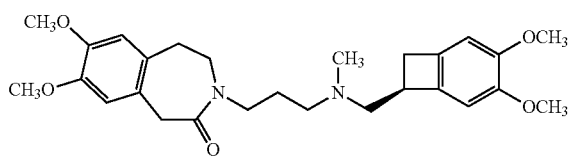

(I)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one,
its addition salts with a pharmaceutically acceptable acid and their hydrates.

Ivabradine, and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of the hydrochloride of ivabradine using as starting material the compound of formula (II):

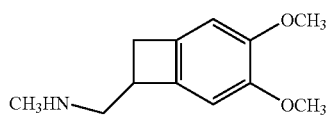

(II)

which is resolved to yield the compound of formula (III):

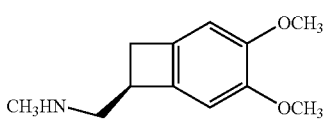

(III)

which is reacted with the compound of formula (IV):

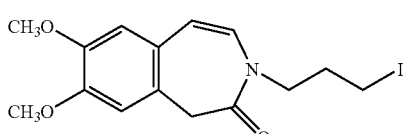

(IV)

to yield the compound of formula (V):

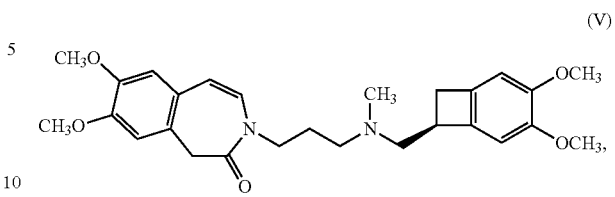

(V)

the catalytic hydrogenation of which yields ivabradine, which is then converted into its hydrochloride.

The drawback of that synthesising method is that only a 1% yield of ivabradine is obtained.

Given the pharmaceutical interest in that compound, it is important to be able to obtain it by an effective synthesising process which results in a good yield of ivabradine.

The present invention relates to a process for the synthesis of a compound of formula (VI) in racemic or optically active form:

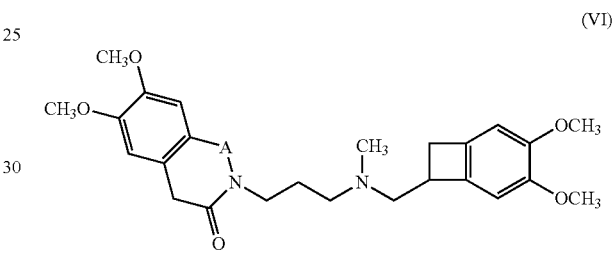

(VI)

wherein A represents $H_2C-CH_2$ or $HC=CH$,
which is characterised in that the compound of formula (VII) in racemic or optically active form:

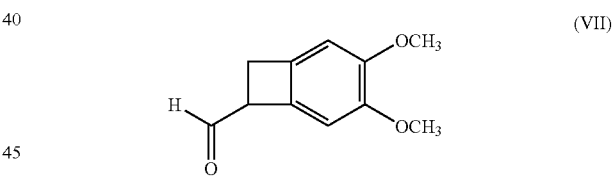

(VII)

is subjected to a reductive amination reaction with a compound of formula (VIII):

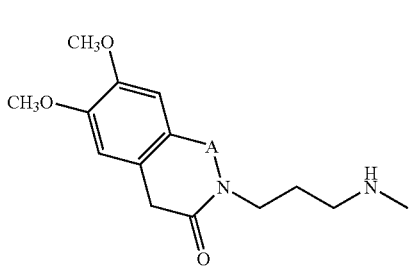

(VIII)

wherein A is as defined hereinbefore,
in the presence of a reducing agent,
in an organic solvent or a mixture of organic solvents.

In a preferred embodiment of the invention, the compound of formula (VII) is in optically active form, and more especially has the (S) configuration.

When A represents H₂C—CH₂, the product of the reductive amination of the compound of formula (VII) having the (S) configuration with a compound of formula (VIII) is ivabradine of formula (I):

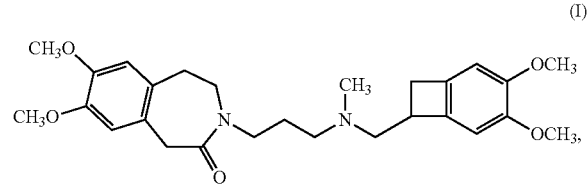

which may optionally be converted into its addition salts with a pharmaceutically acceptable acid selected from hydrochloric acid, hydrobromic, acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into their hydrates.

When A represents HC=CH, the product of the reductive amination of the compound of formula (VII) having the (5) configuration with a compound of formula (VIII) is the compound of formula (V):

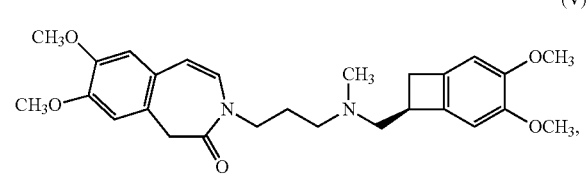

the catalytic hydrogenation of which yields ivabradine of formula (I):

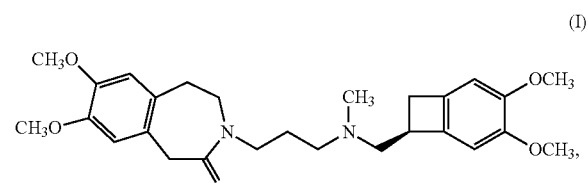

which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into their hydrates.

In another preferred embodiment of the invention, the compound of formula (VII) is in racemic form. The reductive amination reaction of the racemic compound of formula (VII) with a compound of formula (VIII) is in that case followed by an optical resolution step of the compound of formula (VI) obtained.

When A represents H₂C—CH₂, the product obtained after the optical resolution step of the compound of formula (VI) is ivabradine of formula (I):

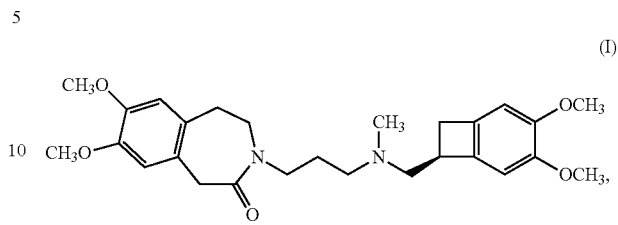

which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into their hydrates.

When A represents HC=CH, the product obtained after the optical resolution step of the compound of formula (VI) is the compound of formula (V):

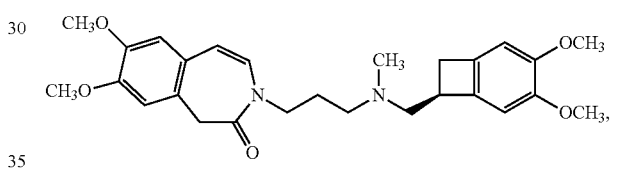

the catalytic hydrogenation of which yields ivabradine of formula (I):

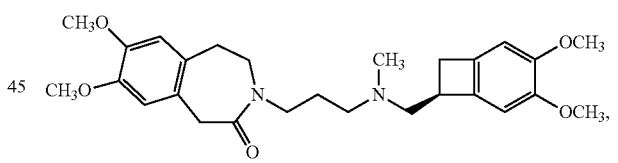

which may optionally be converted into its addition salts with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into their hydrates.

Among the reducing agents that can be used to carry out the reductive amination reaction of the compound of formula (VII) with a compound of formula (VIII) there may be mentioned, without implying any limitation, hydride-yielding compounds or dihydrogen in the presence of a catalyst.

Among the reducing agents that can be used to carry out the reductive amination reaction of the compound of formula (VII) with a compound of formula (VIII) there may be mentioned, without implying any limitation, sodium triacetoxyborohydride, sodium cyanoborohydride and dihydrogen in the presence of a catalyst such as palladium, platinum, nickel, ruthenium, rhodium, and derivatives thereof, especially in supported form or in oxide form.

The reducing agent preferably used to carry out the reductive amination reaction of the compound of formula (VII) with a compound of formula (VIII) is sodium triacetoxyborohydride.

Among the solvents that can be used to carry out the reductive amination reaction of the compound of formula (VII) with a compound of formula (VIII) there may be mentioned, without implying any limitation, tetrahydrofuran, dichloromethane, 1,2-dichloroethane, acetates, alcohols, preferably ethanol, methanol or isopropanol, toluene and xylene.

In a preferred embodiment of the invention, the solvent used to carry out the reductive amination reaction of the compound of formula (VII) with a compound of formula (VIII) is a mixture of organic solvents.

The solvent preferably used to carry out the reductive amination reaction of the compound of formula (VII) with a compound of formula (VIII) is a mixture of tetrahydrofuran and dichloromethane.

The compound of formula (VII), in racemic or optically active form, is a new product which is useful as a synthesis intermediate in the chemical or pharmaceutical industry, especially in the synthesis of ivabradine, its addition salts with a pharmaceutically acceptable acid and their hydrates and, as such, constitutes an integral part of the present invention.

List of the Abbreviations Used:
DMF: N,N-dimethylformamide
THF: tetrahydrofuran
IR: infrared The Examples hereinbelow illustrate the invention.
The melting points (M.p.) were measured on a Köfler block.

EXAMPLE 1

7,8-Dimethoxy-3-[3-(methylamino)propyl]-1,3,4,5-tetrahydro-2H-3-benzazepin-2-one Dissolve 50 g (0.18 mol) of 3-(7,8-dimethoxy-2-oxo-1,2,4,5-tetrahydro-3H-3-benzazepin-3-yl)propanal in 625 ml of methanol. Cool the resulting solution to 0° C. and then add 62.5 ml (0.81 mol; 4.5 equivalents) of an aqueous 40% methylamine solution. Stir for one hour at 0° C. and then add 7.5 g (0.2 mol; 1.1 equivalent) of NaBH$_4$. Stir for 30 minutes at 0° C. and then stir for 12 hours at ambient temperature. Evaporate off the methanol. The residue is taken up in aqueous hydrochloric acid solution (1N), and washed with ethyl acetate. The aqueous phase is then adjusted to pH=8 by adding 20% sodium hydroxide solution and extracted with dichloromethane. The organic phase is washed with water, dried over MgSO$_4$, filtered and then evaporated to dryness to obtain 52 g of an oil, which is purified by flash chromatography on 1.5 kg of silica (eluant=dichloromethane/-ethanol/NH$_4$OH:80/20/2). 42 g of the expected product are obtained in the form of a white solid.
Yield=80%
M.p. (KB)=68-70° C.

EXAMPLE 2

7,8-Dimethoxy-3-[3-(methylamino)propyl]-1,3-dihydro-2H-3-benzazepin-2-one

Step 1: tert-Butyl [3-(7,8-dimethoxy-2-oxo-1,2-dihydro-3H-3-benzazepin-3-yl)propyl]-methylcarbamate Suspend 1.7 g (7.8 mmol) of 7,8-dimethoxy-1,3-dihydro-2H-3-benzazepin-2-one in 35 ml of DMF and then add 374 mg (9.35 mmol, 1.2 equivalents) of sodium hydride (60% suspension in oil). A clear pale yellow solution is obtained, which is stirred for one hour at 25° C. 1.94 g (9.35 mmol, 1.2 equivalent) of tert-butyl (3-chloropropyl)methylcarbamate dissolved in 10 ml of DMF are then added dropwise. The whole is heated at 50° C. overnight and then the solvent is evaporated to dryness. The residue is taken up in water and extracted with dichloromethane. The organic phase is dried over MgSO$_4$, filtered and then evaporated to dryness. 4.2 g of an oil is obtained which is purified by flash chromatography on 200 g of silica (eluant=dichloromethane/ethyl acetate:80/20). 2.3 g of the expected product are obtained in the form of a colourless oil.
Yield=77%
IR (pure): ν=1685, 1659, 1155, 1102, 872, 770 cm$^{-1}$.

Step 2: 7,8-Dimethoxy-3-[3-(methylamino)propyl]-1,3-dihydro-2H-3-benzazepin-2-one Dissolve 1.9 g (4.86 mmol) of the product obtained in Step 1 in 30 ml of ethanol and add to that solution 7 ml (24.3 mmol, 5 equivalents) of HCl in ethanol (3.5N). Heat overnight at 60° C. and evaporate the reaction mixture to dryness. The residue obtained is taken up in water, and the aqueous phase is then adjusted to pH=8 by adding 20% sodium hydroxide solution and extracted with dichloromethane. The organic phase is washed with water, dried over MgSO$_4$, filtered and then evaporated to dryness. 1.1 g of the title product are obtained in the form of a colourless oil.
Yield=78%
IR (pure): ν=3400, 1651, 1610, 1510, 856, 710 cm$^{-1}$.

EXAMPLE 3

3,4-Dimethoxy-bicyclo[4.2.0]octa-1,3,5-triene-7-carbonitrile

The title compound can be obtained by cyclisation of 3-(2-bromo-4,5-dimethoxyphenyl)-propanenitrile as described in the literature (see *Tetrahedron* 1973, 29 73-76) or in accordance with the following reaction sequence:

Step 1: 3,4-Dimethoxy-6-hydroxy-benzaldehyde

In a three-necked flask, disperse 40.8 g of aluminium chloride in 200 ml of dichloromethane with stirring. Cool the solution to 0° C. Pour in dropwise a solution of 20 g (0.101 mol) of 3,4,6-trimethoxybenzaldehyde dissolved in 100 ml of dichloromethane. Allow the temperature to rise again to 19° C. and stir for 45 min. Hydrolyse the reaction mixture with 400 g of water and ice and then add 100 ml of 1N HCl and stir for 30 minutes. Allow to separate and then extract with 200 ml of dichloromethane. The organic phase is washed with 100 ml of 1N HCl, 100 ml of water and 100 ml of saturated aqueous NaCl solution, and then dried over MgSO$_4$, filtered and evaporated to dryness. 16.4 g of title product are obtained.
Yield=77%
IR (pure): 1625, 1146 cm$^{-1}$.

Step 2: 2-Formyl-4,5-dimethoxyphenyl dimethylsulphamate

Dissolve 16.2 g (0.0889 mol) of 3,4-dimethoxy-6-hydroxybenzaldehyde in 80 ml of DMF. Cool to 10° C. and add in portions 24.6 g (0.178 mol) of potassium carbonate. Allow to return to ambient temperature and stir for 30 minutes. Cool to approximately 10° C. and pour in dropwise 10.1 ml (0.093 mol) of N,N-dimethylsulphamoyl chloride. Allow to return to ambient temperature and stir for 2 h. Pour the reaction mixture into 600 g of water and ice and stir for 1 h at ambient temperature. The precipitate formed is filtered off and washed 3 times with 50 ml of water each time and then dried in vacuo. 21.3 g of title product are obtained.

Yield=83%

IR (pure): 1670, 1278, 1150 cm$^{-1}$.

Step 3: 2-(2-Cyanovinyl)-4,5-dimethoxyphenyl dimethylsulphamate

Add 3.1 g (0.0773 mol) of sodium hydride in portions to a solution at 0° C. of 11.9 ml (0.0736 mol) of diethyl cyanomethylphosphonate in 400 ml of THF. Cool the mixture to −10° C. and add dropwise a suspension of 21.3 g (0.0736 mol) of 2-formyl-4,5-dimethoxyphenyl dimethylsulphamate in 200 ml of THF. Stir for 30 minutes and hydrolyse with 600 ml of a solution of sodium hydrogen carbonate and water (50/50) and then extract the solution twice with 300 ml of toluene each time. The organic phase is washed with 100 ml of water and 100 ml of saturated aqueous NaCl solution and then dried over MgSO$_4$, filtered and evaporated to dryness. The residue obtained is crystallised in 80 ml of diisopropyl ether at ambient temperature and then filtered and washed with 20 ml of diisopropyl ether and dried in vacuo. 18.4 g of title product are obtained.

Yield=80%

IR (pure): 2217, 1361, 1165 cm$^{-1}$.

Step 4: 2-(2-Cyanoethyl)-4,5-dimethoxyphenyl dimethylsulphamate

Disperse 6.7 g (0.177 mol) of sodium borohydride in 150 ml of THF. Pour in dropwise a suspension of 18.4 g (0.059 mol) of 2-(2-cyanovinyl)-4,5-dimethoxyphenyl dimethylsulphamate in 200 ml of THF. Pour in dropwise 48 ml of methanol. Heat for 3 h at 50° C. and then cool and add 1 g (0.026 mol) of sodium borohydride. Heat the reaction mixture at 50° C. for 1 h and then stir overnight at ambient temperature. Hydrolyse by pouring into the reaction mixture 60 ml of aqueous 4N HCl solution while maintaining the temperature at approximately 20° C. Add 40 g of ice and 30 ml of water and then extract twice with 200 ml of ethyl acetate each time. The organic phase is washed with water and saturated aqueous NaCl solution and then dried over MgSO$_4$, filtered and evaporated to dryness. 17.4 g of title product are obtained.

Yield=94%

IR (pure): 2246 cm$^{-1}$.

Step 5: 3,4-Dimethoxybicyclo[4.2.0]octa-1,3,5-triene-7-carbonitrile

Under nitrogen, mix together 5.4 ml (0.0382 mol) of redistilled diisopropylamine and 60 ml of THF. Cool the mixture to −50° C. and pour in dropwise 15.3 ml (0.0382 mol) of a 2.5N solution of butyllithium in hexane. Allow the temperature to rise again to −5° C. and stir for 10 minutes. Cool the solution to −60° C. and pour in dropwise a solution of 3 g (0.00954 mol) of 2-(2-cyanoethyl)-4,5-dimethoxyphenyl dimethylsulphamate in 35 ml of THF. Allow the temperature slowly to rise again to −24° C. while monitoring by HPLC disappearance of the reactant. Add the reaction mixture to a mixture of water and ice and extract with ethyl acetate. Wash the organic phases in succession with 1N sodium hydroxide solution, aqueous 1N HCl solution, water and saturated aqueous NaCl solution and then dry them over MgSO$_4$, filter, and evaporate off the solvents. 2 g of residue are obtained which is purified by flash chromatography on 70 g of silica (eluant=dichloromethane) to yield 0.9 g of title product in the form of a white solid.

Yield=50%

M.p. (KB)=89-91° C.

EXAMPLE 4

(R,S)-3,4-Dimethoxy-bicyclo[4.2.0]octa-4,3,5-triene-7-carbaldehyde 10 g (52.8 mmol) of 3,4-dimethoxy-bicyclo[4.2.0]octa-1,3,5-triene-7-carbonitrile are dissolved in 100 ml of anhydrous toluene. The solution is cooled to −78° C. and then 55 ml of diisobutylaluminum hydride solution (1.2M in toluene) are added dropwise while maintaining the temperature below −65° C. (addition time=45 minutes). Stirring is carried out for 1 hour at −78° C. once the addition is complete. Hydrolysis is carried out by adding dropwise 20 ml of methanol. The temperature is allowed to return to −30° C. and then the reaction mixture is added to 200 ml of HCl (0.1N) and extraction with ether is carried out twice. The organic phase is washed in succession with water and saturated aqueous NaCl solution and then dried over MgSO$_4$, filtered and evaporated to dryness to obtain 8 g of title product in the form of pale yellow oil.

Yield=79%

IR (pure): ν=2714, 2630, 1712 cm$^{-1}$.

EXAMPLE 5

(R,S)-3-(3-{[(3,4-Dimethoxybicyclo[4.2.0]octa-1,3,5-trien-7-yl)methyl](methyl)amino}propyl)-7,8-dimethoxy-1,3,4,5-tetrahydro-2H-3-benzazepin-2-one 8 g (52.4 mmol, 1.2 equivalent) of (R,S)-3,4-dimethoxy-bicyclo[4.2.0]octa-1,3,5-triene-7-carbaldehyde are dissolved in a mixture of 150 ml of anhydrous THF and 20 ml of dichloromethane. 12.8 g (43.6 mmol) of 7,8-dimethoxy-3-[3-(methylamino)propyl]-1,3,4,5-tetrahydro-2H-3-benzazepin-2-one and 2.48 ml (43.6 mmol) of acetic acid are added. The whole is cooled to 0° C. and stirred for 30 minutes. 14 g (65.6 mmol, 1.5 equivalent) of sodium triacetoxyborohydride are then added. The reaction is instantaneous. Evaporation to dryness is carried out. The residue is then taken up in 1N sodium hydroxide solution and extracted with dichloromethane. The organic phase is washed with water, dried over MgSO$_4$, filtered and evaporated to dryness to obtain 20 g of an oil, which is purified by flash chromatography on 800 g of silica (eluant=dichloromethane/ethanol/NH$_4$OH:90/10/1). 16.8 g of title product are obtained in the form of a colourless oil, which crystallises at ambient temperature.

Yield=82%

M.p. (KB)=98-100° C.

EXAMPLE 6

3-{3-[{[(7S)-3,4-Dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one hydrochloride 2.1 g of the racemic compound obtained in Example 5 are separated on a 60 cm×60 mm column packed with 2.1 kg of Chiralpak® AD phase (granulometry 20 µm). The eluant used is an ethanol/acetonitrile/diethylamine mixture (10/90/0.1 by volume) at a flow rate of 50 ml/min. The associated ultra-violet detector is used at a wavelength of 280 nm.

0.95 g of the enantiomer having the (R) configuration is obtained in the form of white meringue and then 0.95 g of the enantiomer having the (5) configuration is obtained, likewise in the form of white meringue.

The hydrochloride of the enantiomer having the (S) configuration is then obtained by following the procedure described in patent specification EP 0 534 859 (Example 2, Step E).

EXAMPLE 7

3-{3-[[(3,4-Dimethoxybicyclo[4.2.0]octa-1,3,5-trien-7-yl)methyl]-(methyl)amino]propyl}-7,8-dimethoxy-1,3-dihydro-2H-3-benzazepin-2-one Dissolve 1.1 g (3.78 mmol) of 7,8-dimethoxy-3-[3-(methylamino)propyl]-1,3-dihydro-2H-3-benzazepin-2-one in 50 ml of THF and 7 ml of dichloromethane. Add 0.69 g (4.53 mmol, 1.2 equivalent) of 3,4-dimethoxybicyclo[4.2.0]octa-1,3,5-triene-7-carbaldehyde and 0.22 ml of acetic acid. Cool the reaction mixture to 0° C. and add 1.2 g (5.67 mmol, 1.5 equivalent) of sodium triacetoxyborohydride. The reaction is instantaneous. Evaporate to dryness. The residue is taken up in water, and the aqueous phase is adjusted to pH=8 by adding 20% sodium hydroxide solution and extracted with dichloromethane. The organic phase is washed with water, dried over $MgSO_4$, filtered and evaporated to dryness. 1.7 g of an oil is obtained, which is purified by flash chromatography on 100 g of silica (eluant=dichloromethane/ethanol/$NH_4OH$:95/5/0.5) to yield 1.4 g of title product in the form of a colourless oil.

Yield=79%

IR (pure): ν=1656, 1607, 1511, 1273, 1206, 1102, 836, 760 $cm^{-1}$.

EXAMPLE 8

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride 1.4 g of the racemic compound obtained in Example 7 are separated on a 60 cm×60 mm column packed with 3 kg of Chiralpak® T101 phase (granulometry 20 µm). The eluant used is an ethanol/acetonitrile/diethylamine mixture (10/90/0.1 by volume) at a flow rate of 100 ml/min. The associated ultra-violet detector is used at a wavelength of 280 nm. 0.56 g of the enantiomer having the (R) configuration is obtained in the form of a colourless oil, then 0.62 g of the enantiomer having the (5) configuration is obtained, likewise in the form of a colourless oil.

The compound having the (S) configuration is then hydrogenated by following the procedure described in patent specification EP 0 534 859 (Example 1, Step D). The hydrochloride of the compound obtained is prepared by following the procedure described in patent specification EP 0 534 859 (Example 2, Step E).

EXAMPLE 9

3-{3-[{[(7S)-3,4-Dimethoxybicyclo[4.2.0]octa-1,3,5-trien-7-yl]-methyl}(methyl)amino]propyl}-7,8-dimethoxy-1,3,4,5-tetrahydro-2H-3-benzazepin-2-one hydrochloride By proceeding as in Example 5, starting from (75)-3,4-dimethoxy-bicyclo[4.2.0]octa-1,3,5-triene-7-carbaldehyde and 7,8-dimethoxy-3-[3-(methylamino)propyl]-1,3,4,5-tetrahydro-2H-3-benzazepin-2-one, ivabradine base is obtained, which is then converted into its hydrochloride by following the procedure described in patent specification EP 0 534 859 (Example 2, Step E).

EXAMPLE 10

3-{3-[{[(7S)-3,4-Dimethoxybicyclo[4.2.0]octa-1,3,5-trien-7-yl]methyl}(methyl)amino]propyl}-7,8-dimethoxy-1,3,4,5-tetrahydro-2H-3-benzazepin-2-one hydrochloride By proceeding as in Example 7, starting from (75)-3,4-dimethoxy-bicyclo[4.2.0]octa-1,3,5-triene-7-carbaldehyde and 7,8-dimethoxy-3-[3-(methylamino)propyl]-1,3-dihydro-2H-3-benzazepin-2-one, a compound is obtained which is hydrogenated by following the procedure described in patent specification EP 0 534 859 (Example 1, Step D) to yield ivabradine base, which is then converted into its hydrochloride by following the procedure described in patent specification EP 0 534 859 (Example 2, Step E).

The invention claimed is:

1. A process for the synthesis of a compound of formula (VI) in racemic or optically active form:

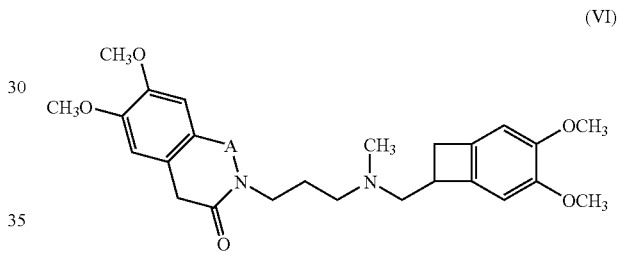

(VI)

wherein A represents $H_2C$—$CH_2$ or HC=CH,
wherein a compound of formula (VII) in racemic or optically active form:

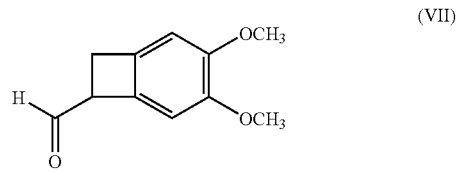

(VII)

is subjected to a reductive amination reaction with a compound of formula (VIII):

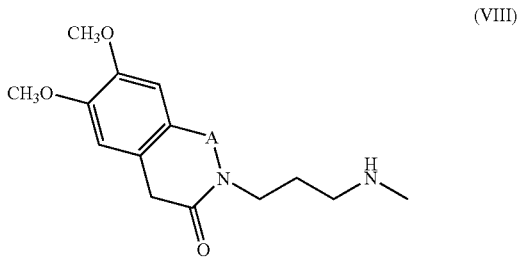

(VIII)

in the presence of a reducing agent,
in an organic solvent or a mixture of organic solvents.

2. The process of claim 1, wherein the compound of formula (VII) is in optically active form.

3. The process of claim 2, wherein the compound of formula (VII) has the (S) configuration.

4. The process of claim 2, wherein the group A represents H₂C—CH₂ and the product of the reductive amination reaction of the compound of formula (VII) with the compound of formula (VIII) is ivabradine of formula (I):

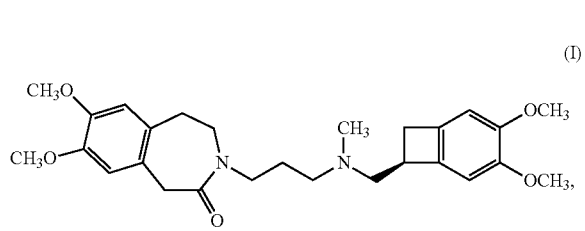

which may optionally be converted into an addition salt with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, which may optionally be converted into a hydrate.

5. The process of claim 2, wherein the group A represents HC=CH and the product of the reductive amination reaction of the compound of formula (VII) having the (S) configuration with the compound of formula (VIII) is the compound of formula (V):

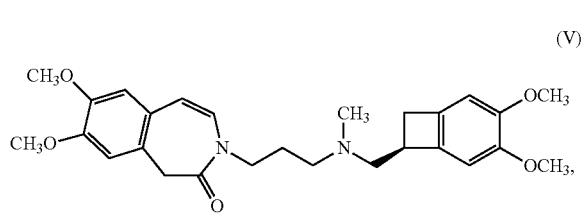

the catalytic hydrogenation of which yields ivabradine of formula (I):

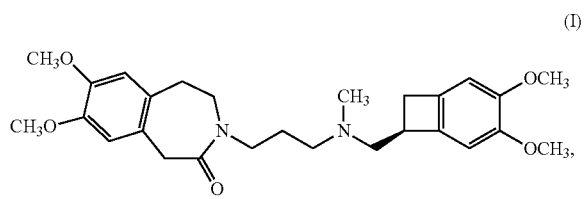

which may optionally be converted into an addition salt with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, which may optionally be converted into a hydrate.

6. The process of claim 1, wherein the compound of formula (VII) is in racemic form and the reductive amination reaction of the compound of formula (VII) with the compound of formula (VIII) is followed by an optical resolution step of the racemic compound of formula (VI) obtained.

7. The process of claim 6, wherein A represents H₂C—CH₂ and the product obtained after the optical resolution step of the compound of formula (VI) is ivabradine of formula (I):

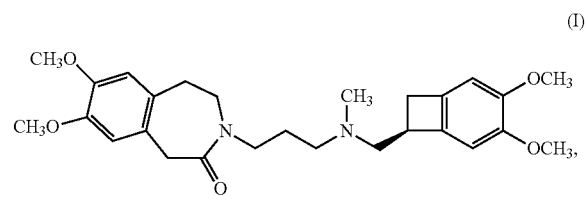

which may optionally be converted into an addition salt with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, which may optionally be converted into a hydrate.

8. The process of claim 6, wherein A represents HC=CH and the product obtained after the optical resolution step of the compound of formula (VI) is the compound of formula (V):

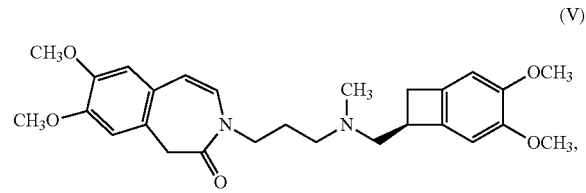

the catalytic hydrogenation of which yields ivabradine of formula (I):

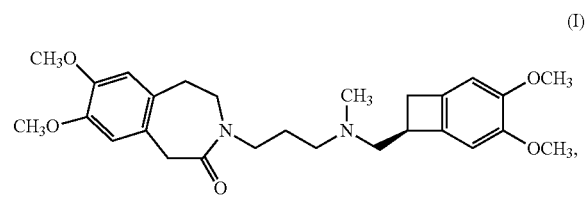

which may optionally be converted into an addition salt with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, which may optionally be converted into a hydrate.

9. The process of claim 1, wherein the reducing agent used to carry out the reductive amination reaction of the compound of formula (VII) with the compound of formula (VIII) is selected from sodium triacetoxyborohydride, sodium cyanoborohydride and dihydrogen in the presence of a catalyst such as palladium, platinum, nickel, ruthenium, rhodium, and derivatives thereof, including in supported form or in oxide form.

10. The process of claim 9, wherein the reducing agent used to carry out the reductive amination reaction of the compound of formula (VII) with a compound of formula (VIII) is sodium triacetoxyborohydride.

11. The process of claim 1, wherein the solvent used to carry out the reductive amination reaction of the compound of formula (VII) with the compound of formula (VIII) is selected from tetrahydrofuran, dichloromethane, 1,2-dichloroethane, acetates, and alcohols.

12. The process of claim 11, wherein the solvent used to carry out the reductive amination reaction of the compound of formula (VII) with the compound of formula (VIII) is selected from ethanol, methanol or isopropanol, toluene and xylene.

13. The process of claim 11, wherein the solvent used to carry out the reductive amination reaction of the compound of formula (VII) with a compound of formula (VIII) is a mixture of tetrahydrofuran and dichloromethane.

14. A compound of formula (VII) in racemic or optically active form:

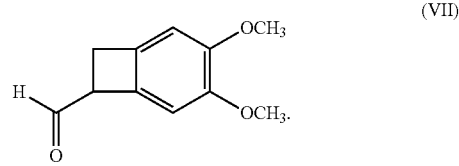

(VII)

* * * * *

UNITED STATES PATENT AND TRADEMARK OFFICE
CERTIFICATE OF CORRECTION

| | | |
|---|---|---|
| PATENT NO. | : 8,097,720 B2 | |
| APPLICATION NO. | : 12/655087 | |
| DATED | : January 17, 2012 | |
| INVENTOR(S) | : Jean-Louis Peglion et al. | |

It is certified that error appears in the above-identified patent and that said Letters Patent is hereby corrected as shown below:

Cover Page, Assignee: "Les Laboratories Servier" should be --Les Laboratoires Servier--.

Signed and Sealed this
Twenty-eighth Day of February, 2012

David J. Kappos
*Director of the United States Patent and Trademark Office*